United States Patent
Schellenberger et al.

(10) Patent No.: US 11,771,780 B2
(45) Date of Patent: Oct. 3, 2023

(54) METHOD FOR PREPARING AN FE-TCDTA CONTRAST AGENT AND PRODUCT OBTAINABLE BY THE METHOD

(71) Applicant: CHARITÉ-UNIVERSITÄTSMEDIZIN BERLIN, Berlin (DE)

(72) Inventors: Eyk Schellenberger, Berlin (DE); Ralf Hauptmann, Berlin (DE); Akvile Haeckel, Lutherstadt Wittenberg (DE); Jing Xie, Berlin (DE); Joerg Schnorr, Oranienburg (DE); Bernd Hamm, Berlin (DE)

(73) Assignee: CHARITÉ-UNIVERSITAETSMEDIZIN BERLIN, Berlin (DE)

(\*) Notice: Subject to any disclaimer, the term of this patent is extended or adjusted under 35 U.S.C. 154(b) by 0 days.

(21) Appl. No.: 17/252,261

(22) PCT Filed: Jun. 6, 2019

(86) PCT No.: PCT/EP2019/064750
§ 371 (c)(1),
(2) Date: Dec. 14, 2020

(87) PCT Pub. No.: WO2020/001950
PCT Pub. Date: Jan. 2, 2020

(65) Prior Publication Data
US 2021/0260223 A1 Aug. 26, 2021

(30) Foreign Application Priority Data
Jun. 27, 2018 (EP) .................................. 18180099

(51) Int. Cl.
*A61K 49/10* (2006.01)
(52) U.S. Cl.
CPC .................. *A61K 49/106* (2013.01)
(58) Field of Classification Search
CPC ....... A61K 49/00; A61K 49/106; A61K 49/10
USPC ................. 424/1.11, 1.65, 9.1, 9.3
See application file for complete search history.

(56) References Cited

U.S. PATENT DOCUMENTS 5,362,475 A 11/1994 Gries et al.

OTHER PUBLICATIONS

Iliuta et al, J. Chem. Eng. Data, vol. 49, pp. 1691-1696 (Year: 2004).*
Iliuta et al, U. Chem. Eng. Data, vol. 49, pp. 1691-1696 (Year: 2004).*
Boehm-Sturm et al, Radiology, Feb. 2018 (Epub Sep. 7, 2017), vol. 286, No. 2, pp. 537-546 (Year: 2017).*
Boehm-Sturm et al (abstract), Radiology, Feb. 2018 (Epub Sep. 7, 2017) (Year: 2017).*
Pietsch et al.: "Long-term retention of gadolinium in the skin of rodents following the administration of gadolinium-based contrast agents", Eur Radiol 2009.
McDonald et al.: "Intracranial Gadolinium Deposition after Contrast-enhanced MR Imaging", Radiology 2015;275 (3):772-782.
Murata et. al: "Macrocyclic and Other Non-Group 1 Gadolinium Contrast Agents Deposit Low Levels of Gadolinium in Brain and Bone Tissue: Preliminary Results From 9 Patients With Normal Renal Function", Invest Radiol 2016; 51 (7):447-453.
White et al.: "Iron (III) Complexes as MRI Contrast Agents", Proc. Int. Soc. Magn. Reson. Med. 1985;1985 (S2):906-909.
Boehm-Sturm et al.: "Low-Molecular-Weight Iron Chelates May Be an Alternative to Gadolinium-based Contrast Agents for T1-weighted Contrast-enhanced MR Imaging", Radiology 2017;170116.

\* cited by examiner

*Primary Examiner* — D. L. Jones
(74) *Attorney, Agent, or Firm* — FOX ROTHSCHILD LLP

(57) ABSTRACT

A process is provided in which the resulting Fe-tCDTA contrast agent has a reduced osmolality. The process according to the invention comprises the following steps:
a) preparing an aqueous solution of tCDTA and FeO(OH), tCDTA and FeO(OH) being present in a molar ratio of from 1:1 to 1:1.4;
b) b.1) adjusting a pH of the aqueous solution to between pH 2.5 and pH 4.5 by adding a base, preferably meglumine, and separating the precipitate; or
b.2) precipitating the Fe-tCDTA contrast agent from the aqueous solution by adding acetone, separating the precipitate, and preparing an aqueous solution from the precipitate; and
c) adjusting a pH of the aqueous solution to between pH 6.5 and pH 8.0 by adding a base, preferably meglumine, and separating the precipitated FeO(OH).

6 Claims, No Drawings

METHOD FOR PREPARING AN FE-TCDTA CONTRAST AGENT AND PRODUCT OBTAINABLE BY THE METHOD

CROSS-REFERENCE TO RELATED APPLICATIONS

This application is a § 371 national phase entry of International Patent Application No. PCT/EP2019/064750, filed on Jun. 6, 2019, which claims priority to and the benefit of European Patent Application No. 18180099.6 filed on Jun. 27, 2018, both of which are hereby incorporated herein by reference in their entireties.

The invention relates to a process for preparing an Fe-tCDTA contrast agent and an Fe-tCDTA contrast agent obtainable by the process.

TECHNICAL BACKGROUND

Low-molecular gadolinium-based contrast agents (GBCA) have become the standard for improving the validity of magnetic resonance imaging (MRI) examinations in all areas of medicine. In 2015, over 10.8 million magnetic resonance imaging (MRI) examinations were carried out in Germany. In about one third of these MRI examinations, GBCA for T1-weighted imaging sequences was applied intravenously, thus enabling improved diagnoses of acute and chronic inflammation, tumours, vascularisation, etc.

Free gadolinium ions are toxic. Due to their chemically similar behaviour compared to calcium ions, they can be incorporated in the liver and bone system, for example, and remain there for years. Since the ion radii of calcium and gadolinium are similar, gadolinium can act as a calcium antagonist and, for example, can inhibit myocardial contractility and the coagulation system.

Although gadolinium ions are toxic, GBCA have been authorised on the condition that they are firmly bound in complexing agents such as DTPA (diethylenetriaminepentaacetic acid) and DOTA (1,4,7,10-tetraazacyclododecane-1,4,7,10-tetraacetic acid) in the authorised drugs and are excreted together with them very quickly and completely, mainly through the kidneys.

However, it has been shown that the excretion may not be complete. For example, a large proportion of recent cases of nephrogenic systemic fibrosis are believed to be due to the toxic effect of incompletely excreted gadolinium contrast agents administered to patients with impaired renal function. Another animal study showed that after administration of GBCA, gadolinium could still be detected in skin biopsies of rats after one year (Pietsch H, Lengsfeld P, Jost G, Frenzel T, Witter J, Sieber M A Long-term retention of gadolinium in the skin of rodents following the administration of gadolinium-based contrast agents. Eur Radiol 2009). The extent of gadolinium accumulation was found to be dependent on the type of complexing agent, especially the stability of the gadolinium complexes.

Especially with repeated administration of low-molecular contrast agents, as is necessary, for example, for breast tumour screening or for monitoring the course of multiple sclerosis, deposits have been found in the brain tissue of healthy people (see, for example, McDonald R J, McDonald J S, Kalimes O F, et al. Intracranial Gadolinium Deposition after Contrast-enhanced MR Imaging. Radiology 2015; 275 (3):772-782). Using ICP-MS, gadolinium deposits of more stable macrocyclic GBCA were also found in samples from deceased patients, especially in bone and brain (Murata N, Gonzalez-Cuyar L F, Murata K, Fligner C, Dills R, Hippe D, Maravilla K R Macrocyclic and Other Non-Group 1 Gadolinium Contrast Agents Deposit Low Levels of Gadolinium in Brain and Bone Tissue: Preliminary Results From 9 Patients With Normal Renal Function. Invest Radiol 2016; 51(7):447-453)

In the past it could be shown that low-molecular iron complexes (especially Fe-DTPA, Fe-tCDTA (tCDTA=trans-cyclohexanediaminetetraacetic acid) can be used as contrast agent for MRI. Although the relaxivity of these iron complexes is lower compared to GBCA, this disadvantage can be compensated by higher doses (see for example White, Ramos, Huberty R, Brasch R, Engelstad B IRON (III) COMPLEXES AS MRI CONTRAST AGENTS. Proc. Int. Soc. Magn. Reson. Med. 1985; 1985(52):906-909). Due to the large amount of iron in the body (approx. 4 g for an adult) and the systems available for absorption, storage and transport, it can be assumed that the long-term toxicity for iron complexes should be lower than for GBCA. In addition, iron oxide nanoparticles (contrast agents, iron replacement therapy), which in contrast to the almost completely excreted low-molecular contrast agents, remain almost completely in the body after i.v. administration, are generally well tolerated.

It has already been shown that iron complexes are also suitable for typical current applications, such as dynamic contrast-enhanced MRI (DCE-MRI), which is used, for example, in breast tumour diagnostics (Boehm-Sturm P, Haeckel A, Hauptmann R, Mueller S, Kuhl O K, Schellenberger E A Low-Molecular-Weight Iron Chelates May Be an Alternative to Gadolinium-based Contrast Agents for T1-weighted Contrast-enhanced MR Imaging. Radiology 2017; 170116).

U.S. Pat. No. 5,362,475 A describes, among other things, the production of iron-based contrast agents, specifically the sodium or N-methylglucamine salt of an iron(III) complex with tCDTA ligand. The synthesis route described in the patent specification provides for direct precipitation of the iron(III) complexes from an aqueous $FeCl_3$ solution. The disadvantage is that, due to the $FeCl_3$ used, Fe-tCDTA with a high content of chloride ions is produced, the separation of which from the iron(III) complex is technically complex and only insufficiently successful. After neutralisation, this leads to a very high salt concentration and thus high osmolality, which is unfavourable for intravenous injections.

SUMMARY OF THE INVENTION

According to the invention, a manufacturing process is provided, in which the resulting Fe-tCDTA contrast agent has a substantially reduced osmolality. The process according to the invention comprises the following steps a) preparing an aqueous solution of tCDTA and FeO(OH), tCDTA and FeO(OH) being present in a molar ratio of from 1:1 to 1:1.4, preferably 1:1.1 to 1:1.3;

b) b.1) adjusting a pH of the aqueous solution to between pH 2.5 and pH 4.5 by adding a base, preferably meglumine, and separating the precipitate; or b.2) precipitating the Fe-tCDTA contrast agent from the aqueous solution by adding a water-miscible organic solvent, separating the precipitate, and preparing an aqueous solution from the precipitate; and c) adjusting a pH of the aqueous solution to between pH 6.5 and pH 8.0, preferably pH 7 to pH 7.5, by adding a base, preferably meglumine, and separating the precipitated FeO(OH).

The invention is based on the finding that an Fe-tCDTA contrast agent of low osmolality can be obtained by the specific sequence of process steps a) to c).

In step a) an aqueous solution is first prepared from the acidic, multidentate ligand tCDTA and iron(III) hydroxide oxide FeO(OH), which is soluble in an acidic environment. Preferably, the aqueous solution of tCDTA solution and FeO(OH) in step a) is heated for 1 to 3 h at 70 to 100° C., especially 90 to 100° C., after the complete addition of the components. A pH of the aqueous solution is preferably adjusted to between pH 0.1 and pH 2. The preferred pH range of the aqueous solution can be achieved by setting the concentration of the acidic ligand tCDTA accordingly.

The FeO(OH) used in step a) is preferably prepared fresh beforehand, more specifically according to two alternative variants by precipitation i) from an aqueous $Fe(NO_3)_3$ solution with addition of an $NH_4OH$ solution or ii) from an aqueous $FeCl_3$ solution with addition of an NaOH solution. The FeO(OH) freshly produced according to these variants can be almost completely dissolved in an acidic environment, unlike commercially available products.

According to a first variant, step b) is followed by adjusting the pH of the aqueous solution to between pH 2.5 to pH 4.5, preferably pH 3.5 to pH 4.5, by adding a base, for example NaOH and preferably meglumine, and separating any precipitate that may have formed. It has been shown that, in contrast to the low initial pH, a relatively stable Fe-tCDTA complex is pre-formed under these conditions, whereby less iron in the form of FeO(OH) is removed from the reaction during subsequent neutralisation. This intermediate step reduces the salt content and thus also the osmolality of the Fe-tCDTA contrast agent after neutralisation by reducing iron-free tCDTA. Preferably, the aqueous solution of tCDTA solution and FeO(OH) is stirred for 0.5 h or longer, especially 0.5 to 2 h, at room temperature after adjusting the pH.

According to a second variant, in step b), Fe-tCDTA is precipitated from the aqueous solution by adding a water-miscible organic solvent, preferably by adding ethanol, acetonitrile or acetone, particularly preferably by adding acetone, the precipitate is separated, dried, and then an aqueous solution is again produced from the precipitate. Excess FeO(OH) thus remains in solution according to this variant and is separated. The low-salt and acid precipitate of Fe-tCDTA is dissolved again in water for further treatment.

In step c) of the process, by adding a base, for example NaOH and preferably meglumine, a pH of the aqueous solution is adjusted to between pH 6.5 and pH 8.0, preferably pH 7.1 to pH 7.5, especially pH 7.3 to pH 7.4, and precipitated FeO(OH) is separated. The contrast agent can then be isolated from the remaining aqueous solution with a high degree of purity.

The Fe-tCDTA contrast agent available by the process according to the invention is characterised by a high degree of purity and especially low salt content. The Fe-tCDTA contrast agent available by the process shows in particular an osmolality at 0.25 mmol/l in water in relation to the Fe content of less than 700 mOsm/kg, especially 300-700 mOsm/kg. Therefore, the contrast agent is particularly suitable for intravenous injection, especially in higher dosages.

Other preferred embodiments of the invention will become clear from the following description.

DETAILED DESCRIPTION OF THE INVENTION

The preparation of an Fe-tCDTA contrast agent will be explained in further detail below in two examples.

A. Synthesis from a Solution of Ferric Nitrate 20 g of ferric nitrate hexahydrate ($Fe(NO_3)_3.6H_2O$) were dissolved in 100 ml of water (dist.) and filtered. A mixture of 50 ml ammonium hydroxide solution (ammonia water, 28 to 30% by weight in water) and 50 ml water (dist.) was added dropwise to the $Fe(NO_3)_3$ solution at room temperature and with stirring. The resulting insoluble iron(III) hydroxide oxide FeO(OH) was collected by filtration (Büchner funnel) and washed several times with water.

17.1 g tCDTA were dissolved in 40 ml water (dist.). The FeO(OH) was added and the volume of the solution was made up to 100 ml with water (dist.). The solution was heated at 95° C. for about 2 h and stirred. The solution was then cooled, filtered, and the volume was reduced to 20 ml by heating. The iron complexes were precipitated from the reduced solution by adding acetone (approx. 300 ml), and the precipitate was centrifuged and dried.

The precipitate of Fe-tCDTA was dissolved again in water (dist.) and the pH was adjusted to between 7.3 and 7.4 using meglumine, with a relative iron concentration of the solution of 38 mg/ml.

B. Synthesis from a Solution of Ferric Chloride

A solution of 14 g NaOH in 70 ml water (dist.) was added dropwise to a solution of 18.92 g ferric chloride hexahydrate ($FeCl_3.6H_2O$) in 70 ml water (dist.), while stirring. The precipitated iron(III) hydroxide oxide FeO(OH) was separated (centrifugation 3 min at 1000×g) and washed 3 times with water (dist.).

18.22 g tCDTA was suspended in 50 ml water (dist.) and added to the FeO(OH). The mixture was heated to 95° C. for 2 h, with stirring, and after cooling was centrifuged (3 min at 1000×g) and filtered through a 0.45 µm syringe filter.

The pH of the solution obtained was adjusted to 4 using meglumine and stirred for 1 h at room temperature. Any precipitates formed were separated by filtration.

After 1 hour, the pH was adjusted to 7.4 using meglumine and the corresponding precipitate was centrifuged off and filtered.

Within the first 1 to 3 days, FeO(OH) precipitate formed. The solution was left to stand at room temperature for another 12 h. The tCDTA solution was centrifuged (3 min at 1000×g), then removed from the iron(III) hydroxide precipitate and filtered with a 0.2 µm syringe filter. The solution was centrifuged again after 3 days (3 min at 1000×g) to remove remaining traces of iron(III) hydroxide.

Determination of Osmolality

The osmolality indicates the molality of the osmotically active particles in a solution:

$$b_{osm} = \frac{n_{osm}}{m_{sol}}$$

with $n_{osm}$: amount of osmotically active particles
$m_{sol}$: mass of the solvent, here water The osmolality here therefore indicates the number of particles of osmotically active substances per kilogram of water and was determined as follows:

For the osmolality measurements, the freezing point measuring instrument OSMOMAT 030 from Gonotec GmbH was used. To determine the total osmolality in aqueous solutions, comparative measurements of the freezing points of pure water and solutions were carried out. While water has a freezing point of 0° C., a solution with a salt concentration of 1 osmol/kg shows a freezing point of −1.858° C.

This means that one mole of a given non-dissociated substance (6.023×10²³ parts diluted in one kilogram of water) lowers the freezing point of a solution by 1.858° C. The device uses the following definitions to calculate the osmolality: $C_{osm}=\Delta T/K$ with $C_{osm}$=osmolality [osmol/kg], T=freezing point decrease [° C.], K=1,858° C. kg/osmol freezing point constant.

Table 1 below shows the osmolality of the two products of the practical examples determined by this method. For comparison, the osmolality of the common gadolinium contrast agent Magnevist was determined in the same way. Furthermore, Fe-tCDTA was synthesised according to the specification described in U.S. Pat. No. 5,362,475 A and the osmolality was determined.

TABLE 1

| Osmolality [mOsm/kg] at 0.25 mmol/l in water (c in relation to Fe or Gd) | |
|---|---|
| Magnevist (gadopentetate dimeglumine, Gd-DTPA) | 815 |
| Synthesis Fe-tCDTA according to U.S. Pat. No. 5,362,475 | 3030 |
| Fe-tCDTA contrast agent according to synthesis pathway A | 517 |
| Fe-tCDTA contrast agent according to synthesis pathway B | 398 |

As can be seen, the osmolality of the Fe-tCDTA contrast agents obtainable in accordance with the invention is greatly reduced, making them particularly suitable for intravenous injection.

Orienting Toxicity Determinations

In first orienting studies with Fe-tCDTA contrast agent according to synthesis pathway A, which was administered intravenously to rats, the animals tolerated doses of 2 mmol per kg body weight (10 times the typical application dose of 0.2 mmol per kg) very well. The urine values were largely normal. The Fe-tCDTA contrast agent according to synthetic pathway B was even administered at 4 mmol per kg body weight (20 times the typical application dose), which corresponds to about 11 g iron in a person weighing 50 kg. The rats tolerated this dose well and only showed increased protein levels in urine after one and two days. At the follow-up after 14 days, all values were normal.

The invention claimed is:

1. A process for preparing an Fe-tCDTA contrast agent comprising:
   a) preparing an aqueous solution of tCDTA and FeO(OH), wherein tCDTA and FeO(OH) are present in a molar ratio of from 1:1 to 1:1.4 and the pH of the aqueous solution is adjusted to between pH 0.1 and pH 2 to dissolve the FeO(OH);
   b) b1) adjusting a pH of the aqueous solution of tCDTA and FeO(OH) to between pH 2.5 and pH 4.5 by adding a base and separating any precipitate that is formed; or
   b2) precipitating Fe-tCDTA from the aqueous solution by adding a water-miscible organic solvent, separating the Fe-tCDTA precipitate, and preparing an aqueous solution from the Fe-tCDTA precipitate; and
   c) adjusting a pH of the aqueous solution to between pH 6.5 and pH 8.0 by adding a base, separating the precipitated FeO(OH) and isolating Fe-tCDTA from the remaining aqueous solution.

2. The process according to claim 1, in which the FeO(OH) in a) is prepared in advance by precipitation i) from an aqueous $Fe(NO_3)_3$ solution with addition of an $NH_4OH$ solution or ii) from an aqueous $FeCl_3$ solution with addition of an NaOH solution.

3. The process according to claim 1, in which the aqueous solution of tCDTA solution and FeO(OH) in a) is heated to between 70 and 100° C. for 1 to 3 h after the addition of tCDTA and FeO(OH).

4. The process according to claim 1, in which the aqueous solution of tCDTA solution and FeO(OH) in a) is stirred at room temperature for 0.5 h or more after adjusting the pH.

5. The process according to claim 1, wherein the base in b1) is meglumine.

6. The process according to claim 1, wherein the base in c) is meglumine.

* * * * *